United States Patent [19]

Stegmann et al.

[11] Patent Number: 4,863,982
[45] Date of Patent: Sep. 5, 1989

[54] ISOCYANURIC ACID DERIVATIVES

[75] Inventors: Werner Stegmann, Liestal; Eduard Troxler; Peter Hofmann, both of Basle; Hans-Rudolf Meier; Paul Dubs, both of Marly, all of Switzerland

[73] Assignee: Ciba-Geigy Corporation, Ardsley, N.Y.

[21] Appl. No.: 217,100

[22] Filed: Jul. 6, 1988

Related U.S. Application Data

[63] Continuation of Ser. No. 47,758, May 8, 1987, abandoned.

[30] Foreign Application Priority Data

May 12, 1986 [CH] Switzerland ................... 1918/86

[51] Int. Cl.$^4$ ................................................ C08K 5/34
[52] U.S. Cl. ........................................ 524/101; 252/401; 544/221
[58] Field of Search .................... 252/401; 524/101; 544/221

[56] References Cited

U.S. PATENT DOCUMENTS

| | | | |
|---|---|---|---|
| 3,531,483 | 9/1970 | Gilles | 524/101 |
| 3,669,961 | 6/1972 | Gilles | 524/101 |
| 3,669,962 | 6/1972 | Smith et al. | 260/248 NS |
| 3,702,837 | 11/1972 | Gilles | 524/101 |

FOREIGN PATENT DOCUMENTS 2445307 4/1975 Fed. Rep. of Germany.

Primary Examiner—John Kight
Assistant Examiner—Kriellion Morgan
Attorney, Agent, or Firm—Harry Falber

[57] ABSTRACT

Compounds of the formula I

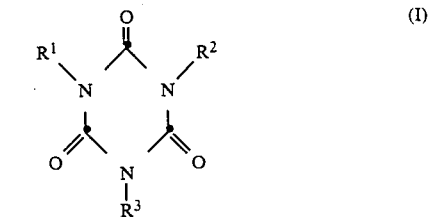

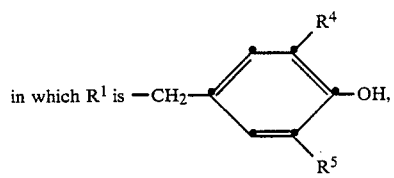

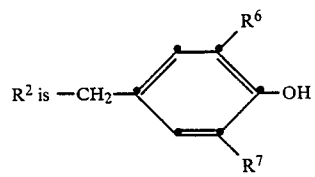

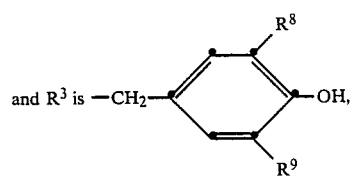

$R^4$ is $C_5$–$C_7$-cycloalkyl which can be substituted by $C_1$–$C_4$-alkyl, and $R^5$ to $R^9$ are independently of one another $C_1$–$C_{18}$ alkyl, unsubstituted or $C_1$–$C_4$-alkyl-substituted $C_5$–$C_7$-cycloalkyl, phenyl, benzyl or allyl, are suitable for stabilizing organic material against thermal, oxidative and/or actinic degradation.

19 Claims, No Drawings

ISOCYANURIC ACID DERIVATIVES

This application is a continuation of application Ser. No. 047,758, filed 5/8/87, now abandoned.

The present invention relates to novel cycloalkyl-p-hydroxybenzyl isocyanurates, to the use thereof for stabilizing organic material and to the organic material stabilized therewith against thermal, oxidative and/or actinic degradation.

p-Hydroxybenzyl isocyanurates and their use for stabilizing organic material are known for example from U.S. Pat. Nos. 3,531,483 and 3,669,962 and German Offenlegungsschrift No. 2,445,307.

The present invention provides compounds of the formula I

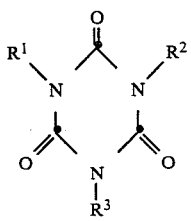

in which $R^1$ is a group of the formula II, $R^2$ is a group of the formula III and $R^3$ is a group of the formula IV

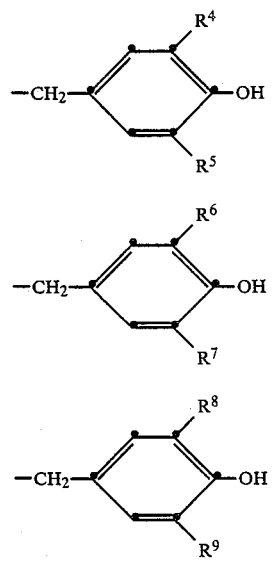

in which $R^4$ is $C_5$–$C_7$-cycloalkyl or $C_1$–$C_4$-alkyl-substituted $C_5$–$C_7$-cycloalkyl, $R^5$, $R^6$, $R^7$, $R^8$ and $R^9$ are independently of one another $C_1$–$C_{18}$-alkyl, $C_5$–$C_7$-cycloalkyl, $C_1$–$C_4$-alkyl-substituted $C_5$–$C_7$-cycloalkyl, phenyl, benzyl or allyl.

Unsubstituted or $C_1$–$C_4$-alkyl-substituted $C_5$–$C_7$-cycloalkyls $R^4$ to $R^9$ are for example cyclopentyl, cyclohexyl, cycloheptyl or 1-methylcyclohexyl. Preference is given to cyclohexyl.

$C_1$–$C_{18}$-alkyls $R^5$ to $R^9$ can be straight-chain or branched radicals. Specific examples are: methyl, ethyl, propyl, isopropyl, n-butyl, sec-butyl, tert-butyl, pentyl, tert-pentyl, hexyl, nonyl, decyl, dodecyl, tetradecyl and hexadecyl. Preference is given to $C_1$–$C_4$-alkyl, in particular methyl, sec-butyl and tert-butyl.

The radicals $R^1$, $R^2$ and $R^3$ can be identical or different.

Preferably $R^1$, $R^2$ and $R^3$ are identical.

Particular preference is given to compounds of the formula I in which $R^1$ is different from $R^2$ and $R^2$ and $R^3$ are identical.

Preference is likewise given to compounds of the formula I in which $R^1$ and $R^2$ are identical and $R^2$ is different from $R^3$.

Interest centres on compounds of the formula I in which $R^1$ is a group of the formula II, $R^2$ is a group of the formula III and $R^3$ is a group of the formula IV, in which the radicals $R^5$ to $R^9$ are independently of one another $C_1$–$C_8$-alkyl, cyclohexyl, 1-methylcyclohexyl, phenyl or allyl.

Interest also centres on compounds of the formula I in which $R^1$ is a group of the formula II, $R^2$ is a group of the formula III and $R^3$ is a group of the formula IV, in which $R^4$ is cyclohexyl or 1-methylcyclohexyl. $R^4$ is preferably cyclohexyl.

A further class of preferred compounds of the formula I are those in which $R^1$ is a group of the formula II, $R^2$ is a group of the formula III and $R^3$ is a group of the formula IV, in which $R^4$ is cyclohexyl and $R^5$ to $R^9$ are independently of one another methyl, tert-butyl, cyclohexyl or phenyl.

Particular preference is given to compounds of the formula I in which $R^1$ is a group of the formula II, $R^2$ is a group of the formula III and $R^3$ is a group of the formula IV, in which $R^4$, $R^6$ and $R^8$ are cyclohexyl and $R^5$, $R^7$ and $R^9$ are identical and are methyl, tert-butyl, cyclohexyl or phenyl.

Interest likewise centres on compounds of the formula I in which $R^1$ is a group of the formula II, $R^2$ is a group of the formula III and $R^3$ is a group of the formula IV, in which $R^5$, $R^7$ and $R^9$ are identical and are methyl or cyclohexyl.

Particular interest centres on compounds of the formula I in which $R^1$ is a group of the formula II, $R^2$ is a group of the formula III and $R^3$ is a group of the formula IV, in which $R^4$, $R^6$ and $R^8$ are cyclohexyl and $R^5$, $R^7$ and $R^9$ are methyl and on those compounds in which $R^4$ to $R^9$ are $C_5$–$C_7$-cycloalkyl or methylcyclohexyl, in particular cyclohexyl.

Examples of compounds of the formula I are:

N,N',N''-tris[3,5-dicyclohexyl-4-hydroxybenzyl]isocyanurate

N,N',N''-tris[3-cyclohexyl-5-methyl-4-hydroxybenzyl]isocyanurate

N,N',N''-tris[3-cyclohexyl-5-tert-butyl-4-hydroxybenzyl]isocyanurate

N,N'-bis[3,5-dicyclohexyl-4-hydroxybenzyl]N''-(3,5-di-tert-butyl-4-hydroxybenzyl) isocyanurate N,N'-bis[3-cyclohexyl-5-methyl-4-hydroxybenzyl]N''-(3,5-di-tert-butyl-4-hydroxybenzyl) isocyanurate N,N'-bis[3-cyclohexyl-5-tert-butyl-4-hydroxybenzyl]-N''-(3,5-di-tert-butyl-4-hydroxybenzyl) isocyanurate N,N'-bis[3,5-dicyclohexyl-4-hydroxybenzyl]N''-(3-tert-butyl5-methyl-4-hydroxybenzyl) isocyanurate N,N'-bis[3-cyclohexyl-5-methyl-4-hydroxybenzyl]N''-(3-tert-butyl-5-methyl-4-hydroxybenzyl) isocyanurate N,N'-bis[3-cyclohexyl-5-tert-butyl-4-hydroxybenzyl]-N''-(3-tert-butyl-5-methyl-4-hydroxybenzyl) isocyanurate N,N'-bis[3,5-dicyclohexyl-4-hydroxybenzyl]N''-(3,5-dimethyl-4-hydroxybenzyl) isocyanurate N,N'-bis[3-cyclohexyl-5-methyl-4-hydroxybenzyl]N''-(3,5-dimethyl-4-hydroxybenzyl) isocyanurate N,N'-bis[3-cyclohexyl-5-tert-butyl-4-hydroxybenzyl]-N''-(3,5-dimethyl-4-hydroxybenzyl) isocyanurate N,N'-bis[3,5-di-tert-butyl-4-hydroxybenzyl]N''-[3,5-dicyclohexyl-4-hydroxybenzyl]isocyanurate N,N'-bis[3,5-di-tert-butyl-4-hydroxybenzyl]N''-[3-cyclohexyl5-methyl-4-hydroxybenzyl]isocyanurate N,N'-bis[3,5-di-tert-butyl-4-hydroxybenzyl]N''-[3-cyclohexyl5-tert-butyl-4-hydroxybenzyl] isocyanurate N,N'-bis[3-tert-butyl-5-methyl-4-hydroxybenzyl]N''-[3,5-dicyclohexyl-4-hydroxybenzyl] isocyanurate N,N'-bis[3-tert-butyl-5-methyl-4-hydroxybenzyl]N''-[3-cyclohexyl-5-methyl-4-hydroxybenzyl]isocyanurate N,N'-bis[3-tert-butyl-5-methyl-4-hydroxybenzyl]N''-[3-cyclohexyl-5-tert-butyl-4-hydroxybenzyl]isocyanurate N,N'-bis[3,5-dimethyl-4-hydroxybenzyl]N''-[3,5-dicyclohexyl4-hydroxybenzyl]isocyanurate N,N'-bis[3,5-dimethyl-4-hydroxybenzyl]N''-[3-cyclohexyl-5-methyl-4-hydroxybenzyl] isocyanurate N,N'-bis[3,5-dimethyl-4-hydroxybenzyl]N''-[3-cyclohexyl-5-tert-butyl-4-hydroxybenzyl] isocyanurate.

Particularly preferred compounds of the formula I are:

N,N',N''-tris[3,5-dicyclohexyl-4-hydroxybenzyl-]isocyanurate

N,N',N''-tris[3-cyclohexyl-5-methyl-4-hydroxybenzyl] isocyanurate

N,N',N''-tris[3-cyclohexyl-5-tert-butyl-4-hydroxybenzyl]isocyanurate

N,N'-bis[3,5-dicyclohexyl-4-hydroxybenzyl]N''-(3,5-di-tert-butyl-4-hydroxybenzyl) isocyanurate N,N'-bis[3,5-di-tert-butyl-4-hydroxybenzyl]N''-[3,5-dicyclohexyl-4-hydroxybenzyl]isocyanurate N,N'-bis[3-cyclohexyl-5-methyl-4-hydroxybenzyl]N''-(3,5-di-tert-butyl-4-hydroxybenzyl) isocyanurate N,N'-bis[3,5-di-tert-butyl-4-hydroxybenzyl]N''-[3-cyclohexyl5-methyl-4-hydroxybenzyl] isocyanurate.

The compounds of the formula I can be prepared in a manner known per se, for example as described in U.S. Pat. Nos. 3,669,961 and 3,669,962, by reacting a phenol of the formula V or mixtures of phenols of the formulae V, VI and VII

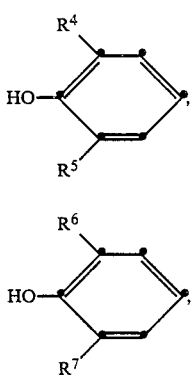

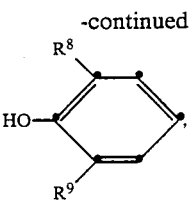

in which $R^4$ to $R^9$ are as defined in the preceding disquisitions, with isocyanuric acid and formaldehyde or a formaldehyde-liberating compound.

Preferably the reagents are used in a stoichiometric ratio.

It is advantageous to carry out the reaction under nitrogen or a noble gas, preferably argon, at a temperature between 70° and 180° C. A temperature of about 130° to 150° C. is preferred.

Suitable formaldehyde-liberating compounds are for example formalin solutions, paraformaldehyde or trioxane.

The reaction can be carried out without a catalyst or in the presence of conventional basic catalysts. Suitable catalysts are secondary and tertiary amines and polyamines, for example diethylamine, tributylamine, ethylenediamine, tetramethylenediamine or hexamethylenetetramine.

The reaction is advantageously effected in an inert organic solvent having a boiling point which is above the reaction temperature. Suitable solvents are for example formamide, acetamide, diethylformamide or preferably dimethylformamide or acetonitrile.

The reaction can also be carried out without a solvent or in an inert solvent or solvent mixture having a boiling point which is below the reaction temperature, but in that case under pressure.

It is in addition advantageous if water is present in the reaction medium.

If mixtures of phenols of the formulae V, VI and VII are used, the products obtained are mixtures of isocyanurates, the separation of which can be effected in a conventional manner, for example by column chromatography or fractional crystallization.

The starting materials are known (some being commercially available) and can be prepared by known methods. The preparation of 2-alkyl-6-cyclohexylphenols and 2,6-dicyclohexylphenols is described for example in U.S. Pat. No. 3,093,587.

The compounds of the formula I and mixtures thereof are suitable for stabilizing organic materials against thermal, oxidative and/or actinic degradation. Examples of such materials are:

1. Polymers of monoolefins and diolefins, for example polypropylene, polyisobutylene, polybut-1-ene, polymethylpent-1-ene, polyisoprene or polybutadiene as well as polymers of cycloolefins, for example of cyclopentene or norbornene; furthermore polyethylene (which can be crosslinked), for example high density polyethylene (HDPE), low density polyethylene (LDPE), linear low density polyethylene (LLDPE).

2. Mixtures of the polymers mentioned under (1), for example mixtures of polypropylene with polyisobutylene, polypropylene with polyethylene (for example PP/HDPE; PP/LDPE) and mixtures of different types of polyethylene (for example LDPE/HDPE).

3. Copolymers of monoolefins and diolefins with one another or with other vinyl monomers, for example ethylene/propylene copolymers, linear low density polyethylene (LLDPE) and mixtures of the same with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof ionomers, as well as terpolymers of ethylene with propylene and a diene, such as hexadiene, dicyclopentadiene or ethylidenenorbornene; as well as mixtures of such copolymers with one another and with polymers mentioned under (1), for example polypropylene/ethylenepropylene copolymers, LDPE/ethylene-vinyl acetate copolymers, LDPE/ethylene-acrylic acid copolymers, LLDPE/ethylene-vinyl acetate copolymers and LLDPE/ethylene-acrylic acid copolymers.

3a. Hydrocarbon resins (for example $C_5$–$C_9$) including hydrogenated modifications thereof (for example tackifying resins).

4. Polystyrene, poly(p-methylstyrene), poly(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride, styrene/acrylonitrile/methyl acrylate; high impact-resistant mixtures of styrene copolymers and another polymer, for example a polyacrylate, a diene polymer or an ethylene/propylene/diene terpolymer; as well as block copolymers of styrene, for example styrene/butadiene/styrene, styrene/isoprene/styrene, styrene-ethylene/butylene-styrene or styrene-ethylene/propylene-styrene.

6. Graft copolymers of styrene or u-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, as well as mixtures thereof with the copolymers mentioned under (5), which are known for example as ABS, MBS, ASA or AES polymers.

7. Halogen-containing polymers, for example polychloroprene, chlororubber, chlorinated or chlorosulphonated polyethylene, epichlorohydrin homopolymers and copolymers, in particular polymers of halogen-containing vinyl compounds, for example polyvinyl chloride, polyvinylidene chloride, polyvinyl fluoride, polyvinylidene fluoride; as well as the copolymers thereof, such as vinyl chloride/vinylidene chloride, vinyl chloride/vinyl acetate or vinylidene chloride/vinyl acetate.

8 Polymers which are derived from α,β-unsaturated acids and derivatives thereof, such as polyacrylates and polymethacrylates, polyacrylamides and polyacrylonitriles.

9. Copolymers of the monomers mentioned under (8), with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines or acyl derivatives thereof or from acetals, such as polyvinyl alcohol, polyvinyl acetate, stearate, benzoate or maleate, polyvinyl butyral, polyallyl phthalate, polyallylmelamine; as well as their copolymers with olefins mentioned in section 1.

11. Homopolymers and copolymers of cyclic ethers, such as polyalkylene glycols, polyethylene oxide, polypropylene oxide or their copolymers with bisglycidyl ethers.

12. Polyacetals, such as polyoxymethylene, and those polyoxymethylenes which contain comonomers, for example ethylene oxide; polyacetals which are modified with thermoplastic polyurethanes, acrylates or MBS.

13. Polyphenylene oxides and sulphides and mixtures thereof with styrene polymers or polyamides.

14. Polyurethanes which are derived from polyethers, polyesters and polybutadienes with terminal hydroxyl groups on the one hand and aliphatic or aromatic polyisocyanates on the other, as well as precursors thereof.

15. Polyamides and copolyamides which are derived from diamines and dicarboxylic acids and/or aminocarboxylic acids or the corresponding lactams, such as nylon 4, nylon 6, nylon 6/6, 6/10, 6/9, 6/12, 4/6, nylon 11, nylon 12, aromatic polyamides based on m-xylene, diamine and adipic acid; polyamides prepared from hexamethylenediamine and isophthalic and/or terephthalic acid with or without an elastomer as modifier, for example poly-2,4,4-trimethylhexamethyleneterephthalamide, poly-m-phenylene-isophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. And also with EPDM- or ABS-modified polyamides or copolyamides; as well as polyamides undergoing a condensation reaction during processing (RIM polyamide systems).

16. Polyureas, polyimides, polyamide imides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, as well as block polyether esters which are derived from polyethers having hydroxyl end groups; and also polycarbonate- or MBS-modified polyesters.

18. Polycarbonates and polyester carbonates.

19. Polysulphones, polyether sulphones and polyether ketones.

20. Crosslinked polymers which are derived from aldehydes on the one hand and phenols, urea or melamine on the other, such as phenol-formaldehyde, urea-formaldehyde and melamine-formaldehyde resins.

21. Drying and non-drying alkyd resins.

22. Unsaturated polyester resins which are derived from copolyesters of saturated and unsaturated dicarboxylic acids with polyhydric alcohols, as well as vinyl compounds as crosslinking agents, and also their halogen-containing, flame-resistant modifications.

23. Crosslinkable acrylic resins which are derived from substituted acrylic acid esters, for example from epoxyacrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers, such as cellulose, natural rubber, gelatin and their chemically modified polymer homolog derivatives, such as cellulose acetates, propionates and butyrates, or the cellulose ethers, such as methylcellulose; as well as colophony resins and derivatives.

27. Mixtures (polyblends) of the aforementioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

28. Natural and synthetic organic substances which are pure monomeric compounds or mixtures thereof, for example mineral oils, animal or vegetable fats, oils and waxes, or oils, waxes and fats based on synthetic esters (for example phthalates, adipates, phosphates or trimellitates), as well as admixtures of synthetic esters with mineral oils in any desired weight ratio, which are used for example as spin finishes, and aqueous emulsions thereof.

29. Aqueous emulsions of natural or synthetic rubbers, for example natural rubber latex or latexes of carboxylated styrene-butadiene copolymers.

The invention therefore further provides compositions which contain organic material and at least one compound of the formula I.

The organic materials are preferably a synthetic polymer, a natural or synthetic elastomer or a natural or synthetic functional fluid, in particular a synthetic polymer sensitive to thermooxidative and/or light-induced degradation. Polyolefins, for example polypropylene and polyethylene, are particularly preferred organic materials.

Functional fluids are for example hydraulic fluids, lubricants, lubricating oils etc.

In general, the compounds according to the invention are added to the organic material to be stabilized in amounts of 0.01 to 10%, preferably 0.05 to 5%, in particular 0.05 to 0.5%, based on the total weight of the material to be stabilized.

For the stabilization it is also possible to use any mixtures obtained of compounds of the formula I without any separation being necessary. This applies in particular to those compounds in which $R^1$ to $R^3$ are not identical and which are generally obtained from the preparation process in the form of mixtures.

This invention therefore further provides physical mixtures containing at least two compounds of the formula I.

These mixtures can also be prepared by mixing the pure components.

For the stabilization of organic material it can be advantageous to use the compounds according to the invention together with so-called thiosynergists. Thiosynergists are known for use as secondary antioxidants or peroxide-destroyers and belong inter alia in the following classes of substances: mercaptans, thioethers, disulphides, dithiocarbamates and heterocyclic thio compounds. Examples of thiosynergists are the following compounds:

pentaerythritol tetrakis[($\beta$-alkylmercapto)propionate], for example pentaerythritol tetrakis[($\beta$-dodecylmercapto)propionate]; pentaerythritol tetrakis(mercaptoacetate), 1,1,1-trimethylolethane tris(mercaptoacetate), 1,1,1-trimethylolpropane tris(mercaptoacetate), dioleyl 3,3'-thiodipropionate, dilauryl 3,3'-thiodipropionate, ditridecyl 3,3'-thiodipropionate, dimyristyl 3,3'-thiodipropionate, distearyl 3,3'-thiodipropionate, dicyclohexyl 3,3'-thiodipropionate, dicetyl 3,3'-thiodipropionate, dioctyl 3,3'-thiodipropionate, dibenzyl 3,3'-thiodipropionate, laurylmyristyl 3,3'-thiodipropionate, diphenyl 3,3'-thiodipropionate, di-p-methoxyphenyl 3,3'-thiodipropionate, didecyl 3,3'-thiodipropionate, dibenzyl 3,3'-thiodipropionate, diethyl 3,3'-thiodipropionate, lauryl 3-methylmercaptopropionate, lauryl 3-butylmercaptopropionate, lauryl 3-laurylmercaptopropionate, phenyl 3-octylmercaptopropionate, lauryl 3-phenylmercaptopropionate, lauryl 3-benzylmercaptopropionate, lauryl 3-(p-methoxy)phenylmercaptopropionate, lauryl 3-cyclohexylmercaptopropionate, lauryl 3-hydroxymethylmercaptopropionate, myristyl 3-hydroxyethylmercaptopropionate, octyl 3-methoxymethylmercaptopropionate, lauryl 3-hydroxymethylmercaptopropionate, myristyl 3-hydroxyethylmercaptopropionate, octyl 3-methoxymethylmercaptopropionate, dilauryl 3-carboxymethylmercaptopropionate, dilauryl 3-carboxypropylmercaptopropionate, dilauryl 4,7-dithiasebacate, dilauryl 4,7,8,11-tetrathiatetradecanedioate, dimyristyl 4,11-dithiatetradecanedioate, lauryl 3-benzthiazylmercaptopropionate; dialkyl disulphides, for example dioctyl disulphide, didodecyl disulphide, dioctadecyl disulphide; dialkyl sulphides, for example didodecyl sulphide, dioctadecyl sulphide; alkylthiopropionic acids and salts thereof, for example 3-laurylmercaptopropionic acid and its calcium salt or the sulphurcontaining compounds described in Japanese Preliminary Published Applications Sho 47-13,533, Sho 47-24,004, Sho 47-24,541 and Sho 47-24,005.

Preferably the compounds according to the invention are used together with the lauryl or stearyl esters of $\beta$-thiodipropionic acid.

The invention therefore also relates to organic material containing at least one compound of the formula I and a thiosynergist.

The weight ratio of thiosynergist: stabilizer according to the invention can be for example 1:1 to 20:1, preferably 2:1 to 10:1, particularly preferably 3:1 to 7:1.

The stabilized polymer compositions of the invention can additionally also contain various conventional additives, for example:

1. Antioxidants 1.1 Alkylated monophenols, e.g. 2,6-di-tert.butyl-4-methylphenol, 2-tert.butyl-4,6-dimethylphenol, 2,6-di-tert.butyl-4-ethylphenol, 2,6-di-tert.butyl-4-n-butylphenol, 2,6-di-tert.butyl-4-i-butylphenol, 2,6-di-cyclopentyl-4-methylphenol, 2-($\alpha$-methylcyclohexyl)-4,6-dimethylphenol, 2,6-di-octadecyl-4-methylphenol, 2,4,6-tri-cyclohexylphenol, 2,6-di-tert.butyl-4-methoxymethylphenol, 2,6-di-nonyl-4-methylphenol.

1.2 Alkylated hydroquinones, e.g. 2,6-di-tert.butyl-4-methoxyphenol, 2,5-di-tert.butyl-hydroquinone, 2,5-di-tert.amylhydroquinone, 2,6-diphenyl-4-octadecyloxyphenol.

1.3 Hydroxylated thiodiphenyl ethers, e.g. 2,2'-thio-bis(6-tert.butyl-4-methylphenol), 2,2'-thio-bis-(4-octylphenol), 4,4'-thio-bis-(6-tert.butyl-3-methylphenol), 4,4'-thio-bis(6-tert.butyl-2-methylphenol).

1.4 Alkylidene bisphenols, e.g. 2,2'-methylene-bis-(6-tert.butyl-4-methylphenol), 2,2'-methylene-bis-(6-tert.butyl-4-ethylphenol, 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.butylphenol), 2,2'-ethylidenebis-(4,6-di-tert.butylphenol), 2,2'-ethylidene-bis-(6-tert.-butyl-4-isobutylphenol), 2,2'-methylene-bis-[6-(α-methylbenzyl)-4-nonylphenol], 2,2'-methylene-bis-[6-(α,α-dimethylbenzyl)-4-nonylphenol], 4,4'-methylene-bis-(2,6-di-tert.butylphenol), 4,4'-methylene-bis-(6-tert.butyl-2-methylphenol), 1,1-bis-(5-tert.butyl-4-hydroxy-2-methylphenyl)butane, 2,6-bis-(3-tert.butyl-5-methyl-2-hydroxybenzyl)-4methylphenol, 1,1,3-tris-(5-tert.butyl-4-hydroxy-2-methylphenyl)butane, 1,1-bis-(5-tert.butyl-4-hydroxy-2-methylphenyl)-3-n-dodecylmercaptobutane, ethylene glycol bis-3,3-bis(3'-tert.butyl-4'-hydroxyphenyl)-butyrate], bis-(3-tert.-butyl-4-hydroxy-5-methylphenyl)-dicyclopentadiene, bis-[2-(3'-tert.butyl-2'-hydroxy-5'-methylbenzyl)-6-tert.butyl-4-methylphenyl]terephthalate.

1.5 Benzyl compounds, e.g. 1,3,5-tris-(3,5-di-tert.butyl-4-hydroxybenzyl)-2,4,6-trimethylbenzene, bis-(3,5-di-tert.butyl-4-hydroxybenzyl) sulphide, isooctyl 3,5-di-tert.butyl4-hydroxybenzylmercaptoacetate, bis-(4-tert.butyl-3-hydroxy-2,6-dimethylbenzyl)dithiol terephthalate, 1,3,5-tris-(3,5-di-tert.butyl-4-hydroxybenzyl) isocyanurate, 1,3,5-tris(4-tert.butyl-3-hydroxy-2,6-dimethylbenzyl) isocyanurate, dioctadecyl 3,5-di-tert.butyl-4-hydroxybenzylphosphonate, Ca salt of monoethyl 3,5-di-tert.butyl-4-hydroxybenzylphosphonate, 1,3,5-tris-(3,5-dicyclohexyl-4-hydroxybenzyl) isocyanurate.

1.6 Acylaminophenols, e.g. 4-hydroxylauranilide, 4-hydroxystearanilide, 2,4-bis-(octylmercapto)-6-(3,5-di-tert.butyl-4-hydroxyanilino)-s-triazine, octyl N-(3,5-di-tert.butyl-4-hydroxyphenyl)-carbamate.

1.7 Esters of β-(3,5-di-tert.butyl-4-hydroxyhenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, tris-(hydroxyethyl) isocyanurate, N,N'-bis-(hydroxyethyl)-oxamide.

1.8 Esters of β-(5-tert.butyl-4-hydroxy-3-methylphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, tris-(hydroxyethyl) isocyanurate, N,N'-bis-(hydroxyethyl)-oxamide.

1.9 Esters of β-(3,5-dicyclohexyl-4-hydroxyphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, tris-(hydroxyethyl) isocyanurate, N,N'-bis-(hydroxyethyl)-oxamide.

1.10 Amides of β-(3,5-di-tert.butyl-4-hydroxyphenyl)-propionic acid, e.g. N,N'-bis-(3,5-di-tert.butyl-4-hydroxyphenylpropionyl)-hexamethylenediamine, N,N'-bis-(3,5-di-tert.butyl-hydroxyphenylpropionyl)-trimethylenediamine, N,N'-bis-(3,5-di-tert.butyl-4-hydroxyphenylpropionyl)-hydrazine.

2. UV adsorbers and light stabilizers 2.1 2-(2'-Hydroxyphenyl)-benztriazoles, e.g. the 5'-methyl, 3',5'-di-tert.butyl, 5'-tert.butyl, 5'-(1,1,3,3-tetramethylbutyl), 5-chloro-3',5'-di-tert.butyl, 5-chloro-3'-tert.butyl5'-methyl, 3'-sec.butyl-5'-tert.butyl, 4'-octoxy, 3',5'-di-tert.amyl, 3',5'-bis-(α,α-dimethylbenzyl) derivative.

2.2 2-Hydroxybenzophenones, e.g. the 4-hydroxy, 4-methoxy, 4-octoxy, 4-decyloxy, 4-dodecyloxy, 4-benzyloxy, 4,2',4'-trihydroxy, 2'-hydroxy,4,4'-dimethoxy derivative.

2.3 Esters of substituted or unsubstituted benzoic acids, e.g. 4-tert.butyl-phenyl salicylate, phenyl salicylate, octylphenyl salicylate, dibenzoylresorcinol, bis-(4-tert.butylbenzoyl)-resorcinol, benzoylresorcinol, 2,4-di-tert.butylphenyl 3,5-di-tert.butyl-4-hydroxybenzoate, hexadecyl 3,5-di-tert.butyl-4-hydroxybenzoate.

2.4 Acrylates, e.g. ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate, N-(β-carbomethoxy-β-cyanovinyl)-2-methylindoline.

2.5 Nickel compounds, e.g. nickel complexes of 2,2'-thiobis-[4-(1,1,3,3-tetramethylbutyl)-phenol], such as the 1:1 or the 1:2 complex, with or without additional ligands, such as n-butylamine, triethanolamine or N-cyclohexyldiethanolamine, nickel dibutyldithiocarbamate, nickel salts of monoalkyl 4-hydroxy-3,5-di-tert.butylbenzylphosphonates, as of the methyl or ethyl ester, nickel complexes of ketoximes, as of 2-hydroxy-4-methylphenylundecylketonoxime, nickel complexes of 1-phenyl-4-lauroyl-5-hydroxypyrazole, with or without additional ligands.

2.6 Sterically hindered amines, e.g. bis-(2,2,6,6-tetramethylpiperidyl) sebacate, bis-(1;2,2,6,6-pentamethylpiperidyl) sebacate, bis-(1,2,2,6,6-pentamethylpiperidyl) n-butyl-3,5-di-tert.butyl-4-hydroxybenzylmalonate the condensation product of 1-hydroxyethyl-2,2,6,6-tetramethyl-4-hydroxypiperidine and succinic acid, the condensation product of N,N'-bis(2,2,6,6-tetramethyl-4-piperidyl)-hexamethylenediamine and 4-tert.-octylamino-2,6-dichloro-1,3,5-s-triazine, tris-(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)-bis-(3,3,5,5-tetramethyl-piperazinone).

2.7 Oxamides, e.g. 4,4'-di-octyloxyoxanilide, 2,2'-dioctyloxy-5,5'-di-tert.butyl-oxanilide, 2,2'-didodecyloxy-5,5'-di-tert.butyl-oxanilide, 2-ethoxy-2'-ethyloxanilide, N,N'-bis-(3-dimethylaminopropyl)-oxamide, 2-ethoxy-5-tert.butyl2'-ethyloxanilide and its mixture with 2-ethoxy-2'-ethyl5,4'-di-tert.butyl-oxanilide, mixtures of o- and p-methoxy as well as of o- and p-ethoxy-disubstituted oxanilides.

3. Metal-deactivators, e.g. N,N'-diphenyloxamide, N-salicylal-N'-salicyloylhydrazine, N,N'-bis(salicyloyl)-hydrazine, N,N'-bis-(3,5-di-tert.butyl-4-hydroxyphenylpropionyl)-hydrazine, 3-salicyloylamino-1,2,4-triazole, bis-(benzylidene)oxalohydrazide.

4. Phosphites and phosphonites, e.g. triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris-(2,4-di-tert.butylphenyl) phosphite, diisodecyl pentaerythritol diphosphite, bis-(2,4-di-tert-.butylphenyl) pentaerythritol diphosphite, tristearyl sorbitol triphosphite, tetrakis-(2,4-di-tert.butylphenyl) 4,4'-biphenylenediphosphonite, 3,9-bis(2,4-di-tert.butylphenoxy)-2,4,8,10-tetraoxa-3,9-diphosphaspiro[5.5]undecane.

5. Peroxide-destroying compounds, e.g. esters of β-thiodipropionic acid, for example the lauryl, stearyl, myristyl or tridecyl ester, mercaptobenzimidazole, the zinc salt of 2mercaptobenzimidazole, zincdibutyl dithiocarbamate, dioctadecyl disulphide, pentaerythritol tetrakis-(β-dodecylmercapto)-propionate.

6. Polyamide-stabilizers, e.g. copper salts in combination with iodides and/or phosphorus compounds and salts of divalent manganese.

7. Basic costabilizers, e.g. melamine, polyvinylpyrrolidone, dicyanodiamide, triallyl cyanurate, urea derivatives, hydrazine derivatives, amines, polyamides, polyurethanes, alkali metal and alkaline earth metal salts of higher fatty acids, for example Ca-stearate, Zn-stearate, Mg-stearate, Na-ricinoleate, K-palmitate, antimony pyrocatecholate or tin pyrocatecholate.

8. Nucleating agents, e.g. 4-tert.butylbenzoic acid, adipic acid, diphenylacetic acid.

9. Fillers and reinforcing agents, e.g. calcium carbonate, silicates, glass fibres, asbestos, talc, kaolin, mica, barium sulphate, metal oxides and hydroxides, carbon black, graphite.

10. Other additives, e.g. plasticizers, lubricants, emulsifiers, pigments, fluorescent brightening agents, flameproofing agents, antistats, blowing agents.

The weight ratio of stabilizer according to the invention:conventional additive can be for example 1:0.5 to 1:5.

Incorporation of stabilizer substances in the organic material is effected in a manner known per se. The metering in can take place during any processing stage before shaping.

The invention also relates to the use of compounds of the formula I for stabilizing organic material against thermal, oxidative and/or actinic degradation, preferred organic materials having been mentioned above.

The following Examples illustrate the invention in more detail. All percentages are by weight, unless otherwise stated.

EXAMPLE 1

Preparation of N,N',N''-tris-[3,5-dicyclohexyl-4-hydroxybenzyl]isocyanurate (A) At room temperature an apparatus consisting of a sulphonating flask (2.5 l) equipped with a propeller stirrer, an internal thermometer, a reflux condenser and a nitrogen inlet line is charged with
135.5 g (1.05 mol) of cyanuric acid, 853.5 g (3.3 mol) of 2,6-dicyclohexylphenol, 114 g (3.8 mol) of paraformaldehyde, 1.76 g (0.0126 mol) of hexamethylenetetramine, 1176 g (16 mol) of dimethylformamide and 31.5 g (1.75 mol) of water.

The suspension is heated in a nitrogen atmosphere with thorough stirring to about 116° C. and is then boiled under reflux for 24 hours. The end of the reaction is considered to have been reached if less than 2% of 2,6-dicyclohexylphenol are present in the reaction mixture (determination by thin layer chromatography).

The now red, clear solution is cooled down to room temperature and, with slow stirring, is seeded until crystallization sets in. The suspension is then stirred for a further 10 hours or thereabouts, is then cooled down to 0° to 5° C. in the course of 2 hours and is subsequently stirred at that temperature for a further hour.

The product is filtered off with a glass suction filter, is washed with 1000 g of methanol and is dried at 40° C. in a vacuum oven at 20 mbar.

The yield is 610 g (65% of theory).

The product has a melting point of 247° C.

Elemental analysis: Calculated: C 76.6%; H 8.7%; N 4.5%; O 10.2%. Found: C 76.7%; H 8.8%; N 4.7%; O 10.2%.

(B) The apparatus consists of a 500 ml jacketed flask with a steel lid and a vapour tube with cocktap, safety valve, thermocouple and pressure gauge.

The 500 ml flask is charged in succession with 38.7 g (0.3 mol) of cyanuric acid, 244.1 g (0.946 mol) of 2,6-dicyclohexylphenol, 31.3 g (0.99 mol) of 100% (technical-grade) paraformaldehyde, 0.5 g (0.0036 mol) of hexamethylenetetramine, 150 g of dimethylformamide and 9 ml of water.

While stirring, the flask is evacuated at room temperature to 100 mbar and depressurized with argon. This is followed by another evacuation to 20 to 30 mbar, and the flask is sealed by means of the cocktap. The reaction mixture is then heated in the sealed flask to 130° C. in the course of 90 minutes, during which the white suspension dissolves completely at about 120° C. and a pressure of about 800 mbar. The now clear, golden brown solution is then stirred at 130° C. for 2 to 3 hours, during which the pressure rises to about 1800 mbar. The reaction is considered to have ended when less than 2% of 2,6-dicyclohexylphenol are detected in a thin layer chromatogram.

The now reddish brown solution is cooled down to about 100° C., and the flask is opened at atmospheric pressure by way of cocktap and vapour tube. By heating to 130° C. and applying a vacuum of up to 20 mbar, a mixture of dimethylformamide/water is distilled off (about 40 g of distillate having a water content of 50–60%). The now substantially water-free solution is poured into a 1500 ml sulphonating flask. At an internal temperature of about 110° C., 200 ml of rinsing methanol and thereafter a further 150 ml of methanol are added dropwise under reflux. In the course of the addition the internal temperature drops to about 70° C. The solution is seeded. The rapidly crystallizing solution is subsequently stirred at 70° to 72° C. for about 1 hour. The yellow mass of crystals is cooled down to room temperature in the course of about 4 to 5 hours and is subsequently further cooled down to 0° to 5° C. with ice. This is followed by stirring at 0° to 5° C. for 1 hour, and the product is then filtered off on a suction filter.

The filter cake is washed three times with 100 ml of cold methanol until colourless. It is then sucked off and dried at 70° to 80° C. in a vacuum oven.

The yield is 263 g (93% of theory).

The product, which is present in the form of a white powder, has a melting point of 243°–250° C.

EXAMPLE 2

Preparation of N,N',N''-tris[3-cyclohexyl-4-hydroxy-5-methylbenzyl]isocyanurate

A sulphonating flask equipped with a propeller stirrer, a thermometer and reflux condenser is charged with 3.23 g (25 mmol) of cyanuric acid, 14.70 g (77 mmol) of 2-cyclohexyl-6-methylphenol, 2.50 g (83 mmol) of paraformaldehyde, 0.30 g (2.1 mmol) of hexamethylenetetramine and 47.50 g (50 ml) of dimethylformamide.

The suspension is heated with slow stirring to 110° C. in a nitrogen atmosphere and refluxed for 48 hours. The reaction mixture is then cooled down to room temperature, poured onto 150 ml of ice-water and stirred. The white product is filtered off, repeatedly washed with water, dissolved in diethyl ether and extracted with water. Removal of the ether under reduced pressure gives the product in the form of a yellowish foam which is crystallized from aqueous ethanol.

The yield is 14.5 g (78% of theory).

The product, which is present in the form of colourless crystals, has a melting point of 212°–218° C.

Elemental analysis: Calculated: N 5.71%. Found: N 5.31%.

EXAMPLE 3

Preparation of N,N',N''-tris[3-tert-butyl-5-cyclohexyl-4-hydroxybenzyl]isocyanurate Example 2 is repeated, except that the 2-cyclohexyl-6-methylphenol is replaced by a corresponding amount of 2-tert-butyl-6-cyclohexylphenol, affording, after washing with hot hexane, 33.24 g (77% of theory) of a white powder having a melting point of 220° C.

Elemental analysis: Calculated: N 4.87%. Found: N 5.05%.

EXAMPLE 4

The same apparatus as described in Example 2 is charged with 6.45 g (50 mmol) of cyanuric acid, 10.73 g (52 mmol) of 2,6-di-tert-butylphenol, 26.70 g (103 mmol) of 2,6-dicyclohexylphenol, 16.3 g (195 mmol) of 36% formalin solution, 0.50 g (4 mmol) of hexamethylenetetramine and 71.3 g (75 ml) of dimethylformamide.

The suspension is heated with slow stirring to about 110° C. in a nitrogen atmosphere and is refluxed for 42 hours. After cooling down to room temperature, the reaction mixture is poured onto 250 ml of water and thoroughly stirred. The reaction product is filtered off. Working up is effected similarly to Example 3 using 200 ml of 30°–60° C. petroleum ether. The result obtained is a rubbery product and, after recrystallization with 200 ml of petroleum ether, a powder which has a melting point of 127°–131° C.

The yield is 35.4 g (80% of theory).

Elemental analysis: Calculated: N 4.73%. Found: N 4.51%.

EXAMPLE 5

Example 4 is repeated, reacting 6.45 g (50 mmol) of cyanuric acid, 21.25 g (103 mmol) of 2,6-di-tert-butylphenol, 13.44 g (52 mmol) of 2,6-dicyclohexylphenol, 16.3 g (195 mmol) of 36% formalin solution, 0.50 g (4 mmol) of hexamethylenetetramine and 71.3 g (75 ml) of dimethylformamide.

The product is worked up as in Example 4, using diethyl ether. A powder having a melting point of 122° C. is obtained.

The yield is 23 g (54% of theory). Elemental analysis: Calculated: N 5.03% Found: N 5.13%.

EXAMPLE 6

Example 4 is repeated, reacting 6.45 g (50 mmol) of cyanuric acid, 10.73 g (52 mmol) of 2,6-di-tert-butylphenol, 19.60 g (103 mmol) of 2-cyclohexyl-6-methylphenol, 16.3 g (195 mmol) of 36% formalin solution, 0.50 g (4 mmol) of hexamethylenetetramine and 71.3 g (75 ml) of dimethylformamide.

The reaction mixture is cooled down, poured onto 250 ml of water and thoroughly stirred. The product is filtered off and can be further purified by column chromatography over silica-gel. The result obtained is a bright yellow powder having a melting point of 114°–120° C.

The yield is 22.97 g (79% of theory). Elemental analysis: Calculated: N 5.49%. Found: N 5.30%.

EXAMPLE 7

Example 4 is repeated, reacting 6.45 g (50 mmol) of cyanuric acid, 21.25 g (103 mmol) of 2,6-di-tert-butylphenol, 9.90 g (52 mmol) of 2-cyclohexyl-6-methylphenol, 16.3 g (195 mmol) of 36% formalin solution, 0.5 g (4 mmol) of hexamethylenetetramine and 71.3 g (75 ml) of dimethylformamide.

Working up is effected as described in Example 3, affording a rubbery product which, after further recrystallization from hexane, is present in the form of a powder having a melting point of 110°–120° C.

The yield is 21.60 g (56% of theory). Elemental analysis: Calculated: N 5.47%. Found: N 5.75%.

EXAMPLE 8:

Polypropylene powder (melt flow index at 230° C. and a test force of 2.16 kp: 2.3 g/10 min) containing 0.1% of calcium stearate is mixed with the additives listed in Table 1 below and is subsequently kneaded at 200° C. in a Brabend Plastograph for 10 minutes. The material thus obtained is compressed in a press with a surface temperature of 260° C. to 1 mm thick sheets, from which strips 1 cm in width and 8.5 cm in length are blanked. From each sheet, several such strips are suspended in a through-circulation oven heated to 149° C. and are inspected at regular intervals. Oxidative decomposition of these strips is evidenced by yellowing, which starts in the form of a circle. A measure of the stability of the sample is the time to decomposition.

TABLE 1

| Stabilizer | Days in through-circulation oven at 149° C. to decomposition of test specimen |
|---|---|
| none | <1 |
| 0.3% of DSTDP | 8 |
| 0.3% of DSTDP + 0.1% of compound of Example 1A | 91 |

DSTDP = distearyl thiodipropionate

What is claimed is:
1. A compound of the formula I

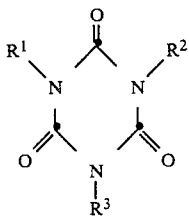

(I)

in which $R^1$ is a group of the formula II, $R^2$ is a group of the formula III and $R^3$ is a group of the formula IV

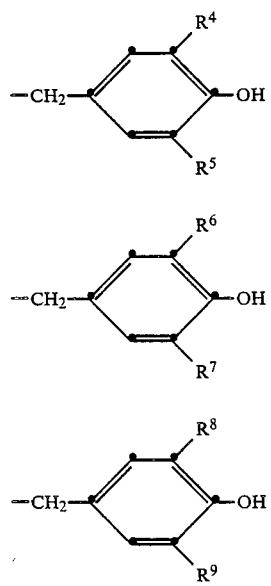

in which $R^4$ is $C_5$-$C_7$-cycloalkyl or $C_1$-$C_4$-alkyl-substituted $C_5$-$C_7$-cycloalkyl, $R^5$, $R^6$, $R^7$, $R^8$ and $R^9$ are independently of one another $C_1$-$C_{18}$-alkyl, $C_5$-$C_7$-cycloalkyl, $C_1$-$C_4$-alkyl-substituted $C_5$-$C_7$-cycloalkyl, phenyl, benzy or allyl.

2. A compound according to claim 1, in which $R^5$ to $R^9$ are independently of one another $C_1$-$C_8$-alkyl, cyclohexyl, 1-methylcyclohexyl, phenyl or allyl.

3. A compound according to claim 1, in which $R^4$ is cyclohexyl or 1-methylcyclohexyl.

4. A compound according to claim 1, in which $R^4$ is cyclohexyl and $R^5$ to $R^9$ are independently of one another methyl, tert-butyl, cyclohexyl or phenyl.

5. A compound according to claim 1, in which $R^1$ to $R^3$ are identical.

6. A compound according to claim 5, in which $R^4$, $R^6$ and $R^8$ are cyclohexyl and $R^5$, $R^7$ and $R^9$ are identical and are methyl, tert-butyl, cyclohexyl or phenyl.

7. A compound according to claim 1, in which $R^1$ is different from $R^2$ and $R^2$ and $R^3$ are identical.

8. A compound according to claim 1, in which $R^1$ and $R^2$ are identical and $R^2$ is different from $R^3$.

9. A compound according to claim 1, in which $R^5$, $R^7$ and $R^9$ are identical and are methyl or cyclohexyl.

10. A compound according to claim 1, in which $R^4$, $R^6$ and $R^8$ are cyclohexyl and $R^5$, $R^7$ and $R^9$ are methyl.

11. A compound according to claim 1, in which $R^4$ to $R^9$ are $C_5$-$C_7$-cycloalkyl or methylcyclohexyl.

12. A compound according to claim 11, in which $R^4$ to $R^9$ are cyclohexyl.

13. The compounds N,N',N''-tris[3-cyclohexyl-5-tert-butyl4-hydroxybenzyl isocyanurate, N,N'-bis[3,5-dicyclohexyl-4hydroxybenzyl]N''-(3,5-di-tert-butyl-4-hydroxybenzyl) isocyanurate, N,N'-bis[3,5-di-tert-butyl-4-hydroxybenzyl]N''(3,5-dicyclohexyl-4-hydroxybenzyl) isocyanurate, N,N'-bis[3-cyclohexyl-5-methyl-4-hydroxybenzyl]N''-(3,5-di-tert-butyl-4-hydroxybenzyl) isocyanurate and N,N'-bis[3,5-di-tert-butyl4-hydroxybenzyl]N''-[3-cyclohexyl-5-methyl-4-hydroxybenzyl]isocyanurate according to claim 1.

14. A composition containing an organic material sensitive to oxidative, thermal and/or actinic degradation and an amount of a compound of the formula I according to claim 1 which is sufficient for stabilization.

15. A composition according to claim 14, in which the organic material is a synthetic polymer, a natural or synthetic elastomer or a natural or synthetic functional fluid.

16. A composition according to claim 14, containing a thiosynergist as additional component.

17. A composition according to claim 14, in which the organic material is a synthetic polymer.

18. A composition according to claim 14, in which the organic material is a polyolefin.

19. A method for stabilizing organic material against thermal, oxidative and/or actinic degradation, which comprises incorporating in the organic material an amount of a compound of the formula I according to claim 1 which is sufficient for stabilization.

* * * * *